US006576633B1

(12) United States Patent
Young et al.

(10) Patent No.: US 6,576,633 B1
(45) Date of Patent: *Jun. 10, 2003

(54) STABLE LIQUID ANTIMICROBIAL SUSPENSION COMPOSITIONS CONTAINING QUARTERNARIES PREPARED FROM HEXAMETHYLENETETRAMINE AND CERTAIN HALOHYDROCARBONS

(75) Inventors: Tracy L. Young, Chesaning; Philip J. Brondsema, Midland, both of MI (US)

(73) Assignee: The Dow Chemical Company, Midland, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/603,846

(22) Filed: Feb. 22, 1996

(51) Int. Cl.$^7$ .................. A01N 43/90; A01N 25/02; A01N 25/04; A01N 25/22
(52) U.S. Cl. ............... 514/244; 514/770; 514/772; 514/970; 514/975; 514/241
(58) Field of Search .................. 514/244, 241, 514/770, 772, 970, 975

(56) References Cited

U.S. PATENT DOCUMENTS

| | | | |
|---|---|---|---|
| 3,148,110 A | 9/1964 | McGahen | 167/26 |
| 3,228,829 A | 1/1966 | Wolf et al. | 167/33 |
| 3,908,009 A | 9/1975 | Polemenakos et al. | 424/249 |
| 4,091,090 A | 5/1978 | Sipos | 424/45 |
| 4,109,002 A | 8/1978 | Davenport et al. | 424/272 |
| 4,197,318 A | 4/1980 | Sipos | 424/326 |
| 4,203,994 A | 5/1980 | Davenport et al. | 424/272 |
| 4,205,065 A | 5/1980 | Wilson | 424/81 |
| 4,352,744 A | 10/1982 | Bettinger et al. | 252/313 S |
| 4,391,647 A | 7/1983 | Deer et al. | 106/115 |
| 4,456,722 A | 6/1984 | Foley | 524/413 |
| 4,548,812 A | 10/1985 | Foley | 424/78 |

OTHER PUBLICATIONS

Farm chemicals Handbook, '95, Meister Publishing Co., Willoughby (Ohio), 1995, pp. C182, C391, C392.*
Applied Microbiology, Charles R. Scott and Paul A. Wolf, vol. 10, pp. 211–216, 1962.
Derwent Abstract #67–04757h, Canadian 799,440 (1968).
Derwent Abstract #72–66003T, Belgium 781603–Q (1972).
Derwent Abstract #66–36018f, Belgium 716373 (1968).
Derwent Abstract #78–53545A/30, Canadian 1034–491 (1978).

* cited by examiner

Primary Examiner—John Pak

(57) ABSTRACT

Anhydrous, liquid antimicrobial compositions comprising quaternaries 1-(benzyl)-3,5,7-triaza-1-azoniaadamantane chloride, 1-(3-chloroallyl)-3,5,7-triaza-1-azoniaadamantane chloride and the cis- and cis/trans-isomers thereof, 1-(α-(2-xylyl))-3,5,7-triaza-1-azoniaadamantane chloride and methyl 1-(3,5,7-triaza-1-azoniaadamantane chloride) acetate in admixture with an anhydrous carrier liquid and a thixotropic material are substantially stable to color changes, physical changes and/or chemical changes while under conventional storage conditions for extended time periods.

9 Claims, No Drawings

STABLE LIQUID ANTIMICROBIAL SUSPENSION COMPOSITIONS CONTAINING QUARTERNARIES PREPARED FROM HEXAMETHYLENETETRAMINE AND CERTAIN HALOHYDROCARBONS

FIELD OF THE INVENTION

The present invention relates to anhydrous, liquid antimicrobial suspension compositions of quaternaries prepared from hexamethylenetetramine and certain halohydrocarbons in admixture with an anhydrous carrier liquid and a thixotropic material. These compositions are chemically, physically and color stable when stored over extended time periods of at least six months.

BACKGROUND OF THE INVENTION

Quaternaries prepared from hexamethylenetetramine and halohydrocarbons are old and well known antimicrobial agents as disclosed in *Applied Microbiology*, Volume 10, pages 211–216, 1962. For example, 1-(benzyl)-3,5,7-triaza-1-azoniaadamantane chloride is prepared from the reaction of hexamethylenetetramine with benzyl chloride; 1-(3-chloroallyl)-3,5,7-triaza-1-azoniaadamantane chloride and the cis- and cis-trans isomers thereof are prepared from the reaction of hexamethylenetetramine with 1,3-dichloropropene; 1-(α-(2-xylyl))-3,5,7-triaza-1-azoniaadamantane chloride is prepared from the reaction of hexamethylenetetramine with α-chloro-2-xylene and 1-(methylacetyl)-3,5,7-triaza-1-azoniaadamantane chloride prepared from the reaction of hexamethylenetetramine with methylchloroacetate.

The compound 1-(3-chloroallyl)-3,5,7-triaza-1-azoniaadamantane chloride is commercially available from The Dow Chemical Company under the trademark DOWICIL™ 200, hereinafter referred to as the "cis-compound," and the various cis-/trans-mixtures of said compound containing from about 50 to 99.5 percent cis-isomer and about 50 to 0.5 percent trans-isomer are commercially available from The Dow Chemical Company under the trademarks DOWICIL™ 100 and DOWICIL™ 75.

The quarternary compounds are particularly effective antimicrobial agents and have been used in products such as, emulsified cutting oils, latexes, latex and emulsion paints, printing inks, glues and adhesives, coatings, sizings, hydraulic fluids and paper pulp dispersions.

Many antimicrobial agents used in cosmetic and personal care formulations, for example, are sold in the form of powder compositions. Formulators who use antimicrobial powder compositions in cosmetic and personal care formulations find themselves further faced with the many handling concerns associated with powders such as dust and mixing problems during product formulation. Many of the known quarternary compound powder compositions cannot conveniently be used in certain personal care products such as hand creams, lotions, shampoos and hand soaps because of mixing and stability problems.

It is therefore often desirable to employ the quarternary compound antimicrobial agents in the form of liquid concentrates since in many situations, liquids are more convenient to handle, and the inherent concerns associated with the use of powders, as mentioned hereinabove, are avoided. Such liquid compositions should be both chemically and physically stable over extended time periods of at least six months under a variety of storage conditions while maintaining their antimicrobial activity. Such compositions should also remain substantially color stable under said storage conditions.

Previous efforts to develop liquid concentrates of quarternary compounds which are homogeneous, color stable, and chemically and physically stable for extended periods of time have been generally unsuccessful. For example, 1-(3-chloroallyl)-3,5,7-triaza-1-azoniaadamantane chloride and its various cis- and trans-mixture are initially antimicrobially active in the presence of water and many other polar solvents, they do not however possess sufficient stability in such polar solutions to remain stable when held under conventional storage conditions for long periods of time.

The known liquid compositions of the cis- or cis/trans-isomers of 1-(3-chloroallyl)-3,5,7-triaza-1-azoniaadamantane chloride have not been found acceptable for commercial use as many of the solvents or carrier liquids employed in these compositions do not provide sufficient stability for said compositions. For example, many organic solvents such as methanol, dimethylformamide, dimethylsulfoxide, monoethanolamine and, propylene glycol methyl ether, and the like, when in a solution, suspension or slurry with the cis-compound or the cis/trans-compounds over a short time form a marked darkening of the color of the composition. This characteristic is particularly unsuitable in the cosmetic industry, latex industry or any other such industry where color is an important parameter.

It is also well known that the quarternary compounds and specifically the cis- and the cis/trans-isomers of 1-(3-chloroallyl)-3,5,7-triaza-1-azoniaadamantane chloride compounds when present in greater than 10 percent by weight in aqueous compositions will darken in color and lose much of their antimicrobial activity after a time period as short as one month. For example, a conventional 30 percent aqueous solution of either the cis- or the cis/trans-compound degrades in color in less than 24 hours after admixture and shows about a 30 percent chemical degradation within one month.

It would be therefore desirable to provide homogeneous, color stable, and chemically and physically stable liquid concentrate compositions containing quarternary compounds and specifically 1-(3-chloroallyl)-3,5,7-triaza-1-azoniaadamantane chloride and its cis- and cis/trans-isomers as active ingredients.

SUMMARY OF THE INVENTION

This invention relates to stable liquid suspension concentrate compositions comprising quaternaries from the group consisting of 1-(benzyl)-3,5,7-triaza-1-azoniaadamantane chloride, 1-(3-chloroallyl)-3,5,7-triaza-1-azoniaadamantane chloride and the cis- and cis/trans isomers thereof, 1-(α-(2-xylyl))-3,5,7-triaza-1-azoniaadamantane chloride and methyl 1-(3,5,7-triaza-1-azoniaadamantane chloride)acetate in admixture with an anhydrous carrier liquid and a thixotropic material as an anti-settling agent.

This invention further relates to stable liquid suspension concentrate compositions comprising a 1-(3-chloroallyl)-3,5,7-triaza-1-azoniaadamantane chloride compound in either the cis or cis/trans-isomer form in admixture with an anhydrous carrier liquid and a thixotropic material as an anti-settling agent. The above compositions are substantially stable to color or chemical degradation and to changes in their physical makeup when they are stored under conventional storage conditions for time periods of up to six months or more.

The suspension compositions of the present invention containing the quaternaries in admixture with the anhydrous carrier liquid and the thixotropic material are liquids which remain substantially color stable for extended periods of at least six months under conventional storage, packaging, and handling conditions.

The liquid suspension concentrate compositions of the present invention are also chemically and physically stable and contain the quaternaries in an amount from about 0.9 to about 75 percent by weight, preferably from about 30 to about 50 percent by weight; the anhydrous carrier liquid is present in an amount from about 25 to about 99 percent by weight; and the thixotropic material is present in an amount from about 0.1 to about 10 percent by weight, preferably from about 0.2 to about 6.0 percent by weight, most preferably from about 0.3 to about 3.0 percent by weight.

As used herein, the term "anhydrous" describes a material composition wherein the color thereof remains substantially the same for the above defined time period having a water content of less than 2.0 percent by weight.

As used herein, the term "color stable" describes a composition wherein the color thereof remains substantially the same for the above defined time period.

As used herein, the term "chemically stable" describes a composition wherein there is substantially no chemical degradation thereof and/or loss of antimicrobial activity for the above-defined time period.

As used herein, the term "physically stable" describes a composition wherein there is substantially no particle separation or settling for the above-defined time period.

The suspension compositions of the present invention are easily handled, and can be employed directly as antimicrobial agents or diluted with conventional inert diluents or substrates, such as water or, alcohols, and the like to prepare ultimate treatment compositions for application to bacteria and fungi or to their habitat.

DETAILED DESCRIPTION OF THE INVENTION

The quaternaries which are the active antimicrobial materials of the present compositions and which are prepared from the reaction of hexamethylenetetramine with 1,3-dichloropropene, benzyl chloride, 2-chloro-α-xylene or methyl chloroacetate are antimicrobially active in the presence of water. These materials, however, have been found to possess insufficient storage stability when made into aqueous concentrate solutions to permit convenient long-term storage and shipping of the concentrates. For example, a concentrated aqueous solution containing more than about 2 percent of either the cis-compound and the cis/trans-compound lose a substantial amount of its biocidal activity under extended storage conditions.

The suspension compositions of the present invention show substantially no color or chemical degradation and demonstrate substantially no loss of antimicrobial activity with storage times of at least six months.

In preparing the suspension compositions of the present invention, the specific order of adding the various ingredients is not critical. In one method, the quaternary compound is mixed in the anhydrous carrier liquid and the thixotrope is added thereto to form a suspension. It is preferred, however, that the quaternary compound is added to a solution of the anhydrous carrier liquid and the thixotrope. Mixing is carried out at ambient temperatures under conditions of high sheer and results in physically stable homogeneous suspensions.

The quaternaries employed in the practice of the present invention are prepared by the reaction of hexamethylenetetramine with either 1,3-dichloropropene, benzyl chloride, 2-chloro-α-xylene or methyl chloroacetate in the presence of a nonaqueous solvent at room temperature. As indicated hereinabove, such preparative procedures are taught in *Applied Microbiology*, Volume 10, pages 211–216, 1962. A conventional method for the preparation of the various cis- and trans-mixtures is found in U.S. Pat. No. 3,228,829. Both of the above references are incorporated herein by reference.

The anhydrous carrier liquids useful in the practice of the present invention are those which do not cause a reduction of antimicrobial activity of the quaternary material and cause no substantial yellowing or color changes of the quaternary-containing composition, nor any chemical changes during storage under conventional conditions for time periods of up to six months or more.

To determine if a specific anhydrous carrier liquid is useful as a carrier liquid, a 30 weight percent solution of one of the quaternaries in the solvent is prepared and stored at room temperature for one month or if a more rapid determination is desired, the solution is held at a temperature of about 45° C. for about one week. The above solutions are analyzed for chemical degradation by HPLC, as hereinafter described, and comparing the sample against a freshly prepared control sample and any chemical degradation should be less than 10 percent for the carrier liquid is to be acceptable. The color of the sample is rated according to the Gardner color scale, as hereinafter described, and if the Gardner color is 3 or less, the solvent can be used; and if it is above 3, the solvent is not acceptable.

Representative carrier liquids include anhydrous surfactants from the alkoxylated alcohols and fatty acids and oil groups such as AETHOXAl™ B, which is PPG-5-Laureth-5, a proprietary product of Henkel Corporation, AEROSURF™ 66E10, which is Isosteareth-10, a proprietary product of Witco Incorporated, CROVOL™ A-40, which is PEG-20 corn glycerides, a proprietary product of Croda Incorporated, GRILLOCAM™ 20, which is Methyl gluceth-20, a proprietary product of Rita Corporation, HEXOTOL™ L-9, which is Laureth-9 and HEXOTOL™ OA-3 Special, which is Oleth-3, these are proprietary products of Heterene Incorporated, IGEPAL™ CO-630, a nonylphenoxypoly(ethyleneoxy)ethanol, which is a proprietary product of Rhone-Poulenc, NOPALCOL™ 4-L, which is PEG 400 monolaurate, NOPALCOL™ 12-R, which is PEG 1200 castor oil, a proprietary product of Henkel Corporation, PEGOSPERSE™ 400DL, which is PEG 400 dilaurate, a proprietary product of Lonza Incorporated, TERGITOL™ 15-S-3 and TERGITOL™ 15-S-9, which are $C_{11}$–$C_{15}$ secondary alcohol ethoxylates and are proprietary products of Union Carbide Corporation; glycerides such as NEOBEE™ M-5, which is caprylic/capric triglyceride, a proprietary product of Stepan Company; polyglycols such as POLYGLYCOL™ BM45-1600, a polyglycol which is a proprietary product of The Dow Chemical Company; RITABATE™ 20, which is polysorbate-20, a proprietary product of Rita Corporation; glycol ethers such as tripropylene glycol methyl ether; or natural fatty oils such as mineral oil, lanolin oil and safflower oil; and other materials such as propylene carbonate, toluene and acetone. The ultimate concentration of the anhydrous carrier liquid in the suspension concentrate is from about 25 weight percent to about 99 weight percent of the surfactant and preferably from about 50 to about 70 weight percent.

The thixotropic materials useful in the practice of the present invention are those which do not cause a reduction of antimicrobial activity of the quaternary material and cause no substantial settling of the quaternary containing concentrate composition during storage under conventional conditions for time periods of up to six months or more.

To determine if a specific thixotropic material is useful, a 30–40 weight percent solution of one of the quaternaries in one of the carrier liquids is prepared. To this solution is added about 1–5 weight percent of the thixotropic material to be tested. The viscosity of the solution is measured at agitator speeds of 10, 20 and 100 RPM. If the viscosity of the solution is increased over that of a control solution consisting only of the quaternary and the carrier liquid, the thixotropic material is acceptable.

Representative thixotropic materials useful in the practice of the present invention include surface treated fumed silicas such as AEROSIL™ R202, which is polymethyl-siloxane hydrophobic fumed silica and AEROSIL™ R805, which is trimethyloctylsilane hydrophobic fumed silica which are proprietary products of Degussa Corporation; organically modified smectite clays such as BENTONE™ 27, a trialkylammonium hectorite, BENTONE™ 34, a tetralkylammonium bentonite, BENTONE™ 38, a tetralkylammonium hectorite, BENTONE™ GEL MIO, a tetralkylammonium hectorite/mineral oil/propylene carbonate mixture and hydrostearate derivatives such as THIXCIN™ R, which is glyceryl tris-12-hydroxystearate and THIXATROL™ ST, a modified glyceryl tris-12-hydroxystearate which are proprietary products of Rheox Inc., CLAYTONE™ APA, a stearalkonium bentonite and FLOWTONE™ R, which is trihydroxysterin, which are proprietary products of Southern Clay Products, Incorporated; SYNCROWAX™ HRSC, a glyceryl tribehenate and calcium behenrate mixture, which is a proprietary product of Croda, Incorporated; TROYTHIX™ XYZ, a castor oil derivative, which is a proprietary product of Troy Corporation. The ultimate concentration of the thixotropic material in the suspension concentrate is from about 0.1 weight percent to about 10 weight percent of the thixotropic material and preferably from about 0.2 to about 6.0 weight percent.

The quaternary compound containing suspension compositions of the present invention can be mixed in a wide variety of products which are subject to microbial attack such as, for example, emulsified cutting oils, latexes, latex and emulsion paints, printing inks, glues and adhesives, coatings, sizings, hydraulic fluids, paper pulp dispersions and cosmetic and personal care formulations.

The suspension compositions are added in amounts sufficient to provide an antimicrobially effective amount of the quaternary compounds in the product.

When the suspension compositions of the present invention are used in personal care items such as shampoos, the suspension compositions can also act as foam boosters and viscosity enhancers. The suspension compositions can also be used in personal care products such as cosmetics including lotions or creams and the like where they can act as emulsifiers, solubilizers and conditioners.

As used herein, the term "antimicrobially-effective amount" refers to that amount of the active quaternary compounds needed to exhibit inhibition of selected microorganisms. Ultimate concentrations of the active compounds in the products to which they are added is from about 0.02 weight percent to about 0.3 weight percent of the active compound and preferably from about 0.1 to about 0.2 weight percent and such amounts are generally suitable for antimicrobial use in most applications. The exact concentration of the compounds to be added to the product may vary within a product type depending upon the specific components of the product and the final uses of the product.

As used herein, the term "microorganism" is meant to refer to bacteria, fungi, viruses, algae, subviral agents and protozoa.

The terms "inhibition", "inhibit" or "inhibiting" as used in the present invention refer to the suppression, stasis, kill, or any other interference with the normal life processes of microorganisms that is adverse to such microorganisms, so as to destroy or irreversibly inactivate existing microorganisms and/or prevent or control their future growth and reproduction.

The present invention is further illustrated by the following examples; however, these examples should not be interpreted as a limitation upon the scope of the present invention.

EXAMPLE 1

A test was carried out to determine the color stability of cis-1-(3-chloroallyl)-3,5,7-triaza-1-azoniaadamantane chloride when it is in admixture with various carrier liquids.

Solutions of the cis-compound in admixture with various carrier liquids were prepared by slowly adding a predetermined amount of the cis compound to a well stirred predetermined amount of the carrier liquid so as to prepare solutions containing 30 percent by weight of the cis compound.

The solutions were aged at room temperature for periods of up to and including six months and then examined to determine any color change or degradation as shown by the Gardner Color Scale. Additionally, a Gardner Color was determined for the carrier liquid containing no cis compound to serve as a carrier liquid control. A cis compound/water solution was also prepared to serve as a water control. The Gardner Color Scale is as follows and the results of these determinations are set forth below in Table 1.

| The Gardner Color Scale | |
|---|---|
| 1. | creamy white or clear in color |
| 2–4. | slight change in color or pale yellow |
| 5–7. | light yellow |
| 8–10. | bright yellow |
| 11–14. | fluorescent dark yellow |

TABLE 1

Gardner color of cis-1-(3-chloroallyl)-3,5,7-triaza-
-1-azoniaadamantane chloride/carrier liquid mixtures
at indicated time periods

| CARRIER LIQUID | CARRIER CONTROL | TIME OF AGING AT ROOM TEMPERATURE | | | |
|---|---|---|---|---|---|
| | | INITIAL | 1 WEEK | 1 MONTH | 6 MONTHS |
| ACETONE | 1 | 1 | 1 | 1 | 1–2 |
| AETHOXAL B | 1 | 1 | 1 | 1 | 1 |

TABLE 1-continued

Gardner color of cis-1-(3-chloroallyl)-3,5,7-triaza-
-1-azoniaadamantane chloride/carrier liquid mixtures
at indicated time periods

| CARRIER LIQUID | CARRIER CONTROL | TIME OF AGING AT ROOM TEMPERATURE | | | |
|---|---|---|---|---|---|
| | | INITIAL | 1 WEEK | 1 MONTH | 6 MONTHS |
| AEROSURF 66E10 | 1 | 1 | 1 | 1 | 1 |
| CROVOL A-40 | 3 | 1–2 | 2–3 | 2–3 | 2–3 |
| DOWANOL TPM | 1 | 1 | 1 | 1 | 1 |
| GRILLOCAM 20 | 3 | 1–2 | 1 | 3 | 3 |
| HETOXAL L-9 | 1 | 1 | 1 | 1 | 1 |
| HETOXAL OA-SPECIAL | 2–3 | 1–2 | 3 | 3 | 2–3 |
| IGEPAL CO-630 | 1 | 1 | 1 | 1 | 1 |
| LANOLIN OIL | 3 | 1–2 | 2–3 | 2–3 | 2–3 |
| MINERAL OIL | 1 | 1 | 1 | 1 | 1 |
| NEOBEE M-5 | 1 | 1 | 1 | 1 | 1 |
| NOPALCOL 4-L | 2–3 | 1–2 | 1 | 1 | 1 |
| NOPALCOL 12-R | 2–3 | 1–2 | 1 | 1 | 1 |
| PEGOSPERSE 400 DL | 1 | 1 | 1 | 1 | 1 |
| POLYGLYCOL BM45-1600 | 1 | 1 | 1 | 1 | 1 |
| PROPYLENE CARBONATE | 1 | 1 | 1 | 1 | 1–2 |
| RITABATE 20 | 3 | 1–2 | 1 | 1 | 2–3 |
| SAFFLOWER OIL | 3 | 1–2 | 1 | 2–3 | 2–3 |
| TERGITOL 15-S-3 | 1 | 1 | 1 | 1 | 1 |
| TERGITOL 15-S-9 | 1 | 1 | 1 | 1 | 1 |
| TOLUENE | 1 | 1 | 1 | 1 | 1 |
| WATER CONTROL | 1 | 1 | 9–10 | 10–12 | 13–14 |

EXAMPLE 2

A test was carried out to determine if there is any chemical degradation of cis-1-(3-chloroallyl)-3,5,7-triaza-1-azoniaadamantane chloride when in admixture with various carrier liquids.

Solutions of the cis-compound in admixture with various carrier liquids were prepared by slowly adding a predetermined amount of the cis compound to a well stirred predetermined amount of the carrier liquid so as to prepare solutions containing 30 percent by weight of the cis-compound. Additionally, a solution of the cis-compound in admixture with water was prepared to serve as a control.

The above solutions were aged at room temperature for one month and then analyzed by high performance liquid chromatography (HPLC) to determine any degradation thereof. The HPLC readings were made on the freshly made cis-compound/carrier liquid solutions and on the same solutions which had been aged for one month. The HPLC was conducted using a Zorbax ODS silica column (4.6 mm×25 cm) and a 50:50 methanol/water mixture as the solvent. The results are set forth below in Table 2 giving both the peak area percentages of the cis-compound/carrier liquid solutions, and the percent loss in area percentages based on the initial HPLC reading of the freshly made cis compound/carrier solution.

TABLE 2

Amount of degradation shown as peak area % of
cis-1-(3-chloroallyl)-3,5,7-triaza-1-
-azoniaadamantane chloride/carrier liquid
mixtures aged for one month as determined by
HPLC

| CARRIER LIQUID | Initial Peak Area % | Peak Area % After One Month of Storage[1] | % Loss in Peak Area Percent from initial Reading |
|---|---|---|---|
| ACETONE | 90.2 | 90.3 | 0.1 |
| AETHOXAL B | 87.4 | 86.4 | −1.1 |
| AEROSURF 66E10 | 87.5 | 92.6 | 7.2 |
| CROVOL A-40 | 89.2 | 88.5 | −0.8 |
| DOWANOL TPM | 87.5 | 88.77 | 1.5 |
| GRILLOCAM 20 | 87.4 | 93.7 | 7.2 |
| HETOXAL L-9 | 92.4 | 91.7 | −0.8 |
| HETOXAL OA-SPECIAL | 95.2 | 90.3 | −5.1 |
| IGEPAL CO-630 | 92.4 | 97.2 | 5.2 |
| LANOLIN OIL | 88.6 | 89.5 | 1.1 |
| MINERAL OIL | 88.5 | 90.96 | 2.8 |
| NEOBEE M-5 | 87.6 | 91.7 | 4.7 |
| NOPALCOL 4-L | 90.5 | 86.7 | −4.2 |
| NOPALCOL 12-R | 84.6 | 86.3 | 2.1 |
| PEGOSPERSE 400 DL | 89.5 | 87.6 | −2.1 |
| POLYGLYCOL BM45-1600 | 87.7 | 88.0 | 0.3 |
| PROPYLENE CARBONATE | 91.5 | 92.2 | 0.8 |
| RITABATE 20 | 84.97 | 80.8 | 7.0 |
| SAFFLOWER OIL | 88.3 | 89.8 | 1.7 |
| TERGITOL 15-S-3 | 88.5 | 92.1 | 4.1 |
| TERGITOL 15-S-9 | 92.4 | 92.8 | 0.4 |
| TOLUENE | 91.4 | 87.1 | −4.7 |
| WATER CONTROL | 88.1 | 70.7 | −19.8 |

[1]: At the time these results were read, the HPLC unit used was a different unit as the original unit was inoperative. This would be the source of anomalies in expected numbers. Relative relations between various carrier liquids are unaffected.

EXAMPLE 3

A test was carried out to determine the color and chemical stability of one of the hereinafter set forth quaternary compound containing suspension compositions in admixture with 69 weight percent IGEPAL CO-630 as the carrier liquid and 1 weight percent AEROSIL R202 as the thixotrope.

The compositions were aged at room temperature for one week and then analyzed by HPLC to determine any degradation thereof. In addition, an unaged solution of cis-1-(3-chloroallyl)-3,5,7-triaza-1-azoniaadamantane chloride in admixture with water only was prepared as a control. The HPLC was conducted using a Zorbax ODS silica column (4.6 mm×25 cm) and a 50:50 methanol/water mixture as the solvent. The results are set forth below in Table 3.

The compositions were also examined to determine any color change as shown by the Gardner Color Scale, defined hereinbefore. The results of these determinations are also set forth below in Table 3.

TABLE 3

Color and/or chemical changes for compositions containing 30 weight percent of a quaternary compound in admixture with IGEPAL CO-630 and AEROSIL R202 which are aged for 1 week at 45° C. prior to being tested

| QUARTERNARY COMPOUND | COLOR CHANGE | CHEMICAL CHANGE |
|---|---|---|
| CIS-1-(3-CHLOROALLYL)-3,5,7-TRIAZA-1-AZONIAADAMANTANE CHLORIDE | no | no |
| 1-(BENZYL)-3,5,7-TRIAZA-1-AZONIAADAMANTANE CHLORIDE | no | no |
| 1-(A-(2-XYLYL))-3,5,7-TRIAZA-1-AZONIAADAMANTANE CHLORIDE | no | no |
| METHYL 1-(3,5,7-TRIAZA-1-AZONIAADAMANTANE CHLORIDE) ACETATE | no | no |
| CIS-1-(3-CHLOROALLYL)-3,5,7-TRIAZA-1-AZONIAADAMANTANE CHLORIDE/WATER CONTROL | yes Gardner 13–14 | yes |

EXAMPLE 4

The antimicrobial activity of cis-1-(3-chloroallyl)-3,5,7-triaza-1-azoniaadamantane chloride in admixture with various carrier liquids is demonstrated by the following techniques.

The antimicrobial activity of the various mixtures is set forth as the minimum inhibitory concentration (MIC) for the test mixture and is determined for nine (9) bacteria using nutrient agar as the growth media. This determination is conducted using test mixtures which have been aged at room temperature for six months and then diluted in water to a one percent dilution in water.

Nutrient agar at a pH of 6.8 is prepared by adding a predetermined amount of nutrient agar to a predetermined amount of deionized water.

The agar is dispensed in 30 mL aliquots into 25×200 mm test tubes, capped and autoclaved for 20 minutes at 121° C. To the tubes containing the molten agar, an appropriate amount of the hereinabove prepared one percent test mixtures is added so that the final concentrations of the test mixtures in the agar are 0, 20, 30, 40, 60, 80, 120, 160, 240, 320 and 480 ppm.

The test tubes are cooled to an agar temperature of 49° C. The contents of the test tubes are then transferred to sterile plastic petri plates and allowed to solidify and age for 24 hours. Each petri plate containing the nutrient agar is inoculated in triplicate with the various bacteria species.

The inoculation with bacteria is accomplished by using the following procedure. Twenty-four hour-cultures of each of the set forth bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per mL of suspension of a particular bacteria. Aliquots of 0.3 mL of each of the bacterial suspensions are used to fill the individual wells of a Steer's Replicator. For each microbial suspension, 0.3 mL was used to fill three wells (i.e., three wells of 0.3 mL each) so that for the nine different bacteria, 27 wells are filled. The Steer's Replicator is then used to inoculate the nutrient agar petri plates.

The inoculated petri plates are incubated at 30° C. for 48 hours and then read to determine the lowest concentration of the test mixture that inhibited all growth of the respective bacteria.

Table 4 lists the bacteria used in the MIC test described above along with their respective American Type Culture Collection (ATCC) identification numbers.

TABLE 4

Bacteria used in the Minimum Inhibitory Concentration Test

| BACTERIA | ATCC No. |
|---|---|
| *BACILLUS SUBTILIS* (BS) | 8473 |
| *ENTEROBACTER AEROGENES* (EA) | 13048 |
| *ESCHERICHIA COLI* (EC) | 11229 |
| *KLEBSIELLA PNEUMONIAE* (KP) | 8308 |
| *PROTEUS VULGARIS* (PV) | 881 |
| *PSEUDONONAS AERUGINOSA* (PA) | 10145 |
| *PSEUDOMONAS AERUGINOSA* PRD-10 (FRD) | 15442 |
| *SALMONELLA CHOLERAESUIS* (SC) | 10708 |
| *STAPHYLOCOCCUS AUREUS* (SA) | 6538 |

In Table 5, the MIC values of the compounds of the present invention as compared to the MIC of a freshly made solution of cis-1-(3-chloroallyl)-3,5,7-triaza-1-azoniaadamantane chloride in water alone to serve as a control, and referred to in Table 5 as "CONTROL". The results are set forth for the bacteria organisms which are listed in Table 4.

TABLE 5

Minimum Inhibitory Concentrations for Test Compounds in Bacteria Species (in ppm)

| CARRIER LIQUID | ORGANISMS | | | | | | | | |
|---|---|---|---|---|---|---|---|---|---|
| | BS | EA | EC | KP | PV | PRD | PA | SC | SA |
| AETHOXAL B | 60 | 60 | 120 | 60 | 60 | 240 | 320 | 160 | 60 |
| AEROSURF 66E10 | 60 | 120 | 120 | 60 | 60 | 240 | 320 | 160 | 60 |
| DOWANOL TPM | 60 | 60 | 80 | 60 | 40 | 240 | 320 | 160 | 60 |
| HETOXAL L-9 | 60 | 80 | 80 | 60 | 60 | 240 | 320 | 160 | 60 |
| HETOXAL OA-SPECIAL | 30 | 80 | 80 | 60 | 60 | 240 | 320 | 160 | 60 |
| IGEPAL CO-630 | 30 | 120 | 120 | 60 | 60 | 240 | 320 | 160 | 60 |
| LANOLIN OIL | 60 | 80 | 120 | 60 | 60 | 240 | 320 | 320 | 60 |
| MINERAL OIL | 60 | 60 | 80 | 60 | 60 | 240 | 320 | 160 | 60 |
| NEOBEE M-5 | 60 | 120 | 120 | 60 | 60 | 240 | 320 | 160 | 60 |
| NOPALCOL 4-L | 30 | 80 | 80 | 60 | 60 | 240 | 320 | 160 | 60 |
| NOPALCOL 12-R | 60 | 120 | 120 | 60 | 60 | 320 | 320 | 240 | 60 |
| POLYGLYCOL BM45-1600 | 60 | 60 | 120 | 60 | 40 | 240 | 240 | 80 | 40 |
| RITABATE 20 | 80 | 80 | 120 | 120 | 60 | 320 | 480 | 240 | 60 |
| SAFFLOWER OIL | 80 | 80 | 80 | 60 | 60 | 320 | 480 | 160 | 60 |
| TERGITOL 15-S-9 | 60 | 80 | 80 | 60 | 60 | 240 | 320 | 120 | 60 |
| CONTROL | 60 | 80 | 80 | 60 | 40 | 240 | 320 | 160 | 60 |

EXAMPLE 5

The antimicrobial activity of a composition mixture consisting of 30 weight percent of cis-1-(3-chloroallyl)-3,5,7-triaza-1-azoniaadamantane chloride in admixture with 69 weight percent IGEPAL CO-630 as the carrier liquid and 1 weight percent AEROSIL R202 as the thixotrope which formulation had been stored for time periods up to and including 9 months is demonstrated by the following procedure.

The antimicrobial activity of the mixture is set forth as the MIC for the mixture and is determined for nine (9) bacteria using nutrient agar as the growth media. This determination is conducted using the test mixture as a one percent dilution in water.

Nutrient agar at a pH of 6.8 is prepared by adding a predetermined amount of nutrient agar to a predetermined amount of deionized water.

The agar is dispensed in 30 mL aliquots into 25×200 mm test tubes, capped and autoclaved for 20 minutes at 121° C. To the tubes containing the molten agar, an appropriate amount of one of the hereinabove prepared one percent test mixtures from test mixtures stored for 1 month, 2 months, 3 months and 9 months, respectively, is added so that the final concentrations in the agar for each test mixture are 0, 20, 30, 40, 60, 80, 120, 160, 240, 320 and 480 ppm. In addition, to a tube containing the molten agar is added a one percent mixture of a freshly prepared solution of cis-1-(3-chloroallyl)-3,5,7-triaza-1-azoniaadamantane chloride in water is prepared to serve as a control.

The test tubes containing the agar are cooled to a temperature of 49° C. The contents of the test tubes are then transferred to sterile plastic petri plates and allowed to solidify and age for 24 hours. Each petri plate containing the nutrient agar is inoculated in triplicate with bacteria.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per mL of suspension of a particular bacteria. Aliquots of 0.3 mL of each of the bacterial suspensions are used to fill the individual wells of Steer's Replicator. For each microbial suspension, 0.3 mL was used to fill three wells (i.e., three wells of 0.3 mL each) so that for the nine different bacteria, 27 wells are filled. The Steer's Replicator is then used to inoculate the nutrient agar petri plates.

The inoculated petri plates are incubated at 30° C. for 48 hours and then read to determine the lowest concentration of the test mixture that inhibited all growth of the respective bacteria set forth in Table 4. The results of this determination is set forth below in Table 6.

TABLE 6

Minimum Inhibitory concentrations for the following bacteria species in ppm for compositions of cis-1-(3-chloroallyl)-3,5,7-triaza-1--azoniaadaniantane chloride in admixture with IGEPAL CO-630 and AEROSIL R202 aged for the indicated time period prior to being tested

| BACTERIA | CONTROL | 1 MONTH[1] | 2 MONTHS | 3 MONTHS | 9 MONTHS[2] |
|---|---|---|---|---|---|
| BS | 60 | 30 | 30 | 30 | 60/60 |
| EA | 60 | 70 | 80 | 80 | 60/80 |

TABLE 6-continued

Minimum Inhibitory concentrations for the following bacteria species in ppm for compositions of cis-1-(3-chloroallyl)-3,5,7-triaza-1--azoniaadaniantane chloride in admixture with IGEPAL CO-630 and AEROSIL R202 aged for the indicated time period prior to being tested

| BACTERIA | CONTROL | 1 MONTH[1] | 2 MONTHS | 3 MONTHS | 9 MONTHS[2] |
|---|---|---|---|---|---|
| EC | 80 | 80 | 80 | 120 | 80/80 |
| KP | 60 | 60 | 60 | 60 | 60/60 |
| PV | 40 | 60 | 40 | 60 | 40/40 |
| PRD | 160 | 160 | 160 | 240 | 240/240 |
| PA | 320 | 400 | 320 | 320 | 320/320 |
| SC | 60 | 45 | 30 | 60 | 160/160 |
| SA | 30 | 30 | 30 | 40 | 40/60 |

[1]average of 2 runs
[2]first number is MIC for the composition; second number is MIC for a fresh control

EXAMPLE 6

The physical stability (suspension stability) of a composition consisting of about 30 weight percent of cis-1-(3-chloroallyl)-3,5,7-triaza-1-azoniaadamantane chloride in admixture with about 69 weight percent IGEPAL CO-630 as the carrier liquid and about 1 weight percent of either AEROSIL R202 or AEROSIL R805 as the thixotrope is demonstrated by the following procedure.

The compositions were allowed to remain undisturbed at room temperature for up to six months and then examined to determine if any settling of particles occurred. In addition, a 30 weight percent solution of cis-1-(3-chloroallyl)-3,5,7-triaza-1-azoniaadamantane chloride in admixture with IGEPAL CO-630 and no thixotrope was prepared to serve as a control. The results of this examination are set forth below in Table 7.

TABLE 7

Particle settling in percent for compositions of cis-1-(3-chloroallyl)-3,5,7-triaza-1--azoniaadamantane chloride in admixture with IGEPAL CO-630 and AEROSIL R202 or AEROSIL R805 for the indicated time period

| THIXOTROPE | 2 DAYS | 1 WEEK | 2 MONTH | 6 MONTHS |
|---|---|---|---|---|
| AEROSIL R202 | 0.0 | 0.0 | 0.0 | 0.0 |
| AEROSIL R805 | 0.0 | 0.0 | 0.0 | — |
| CONTROL | 5.0 | 100 | — | — |

EXAMPLE 7

The physical stability (suspension stability) of compositions consisting of either about 30 weight percent of cis-1-(3-chloroallyl)-3,5,7-triaza-1-azoniaadamantane chloride in IGEPAL CO-630 as the carrier liquid or 40 weight percent of cis-1-(3-chloroallyl)-3,5,7-triaza-1-azoniaadamantane chloride in mineral oil as the carrier liquid when mixed with various thixotrope materials is demonstrated by the following procedure.

Solutions of IGEPAL CO-630 in admixture with a predetermined amount of one of AEROSIL R202, AEROSIL R805, FLOWTONE R, THIXCIN R or THIXATROL ST were prepared. Additionally, solutions of mineral oil in admixture with a predetermined amount of one of BENTONE 27, THIXATROL ST, TROYTHIX XYZ or SYNCROWAX HRS-C were also prepared. To each of the solutions was slowly added a predetermined amount of cis-1-(3-chloroallyl)-3,5,7-triaza-1-azoniaadamantane chloride under high shear mixing conditions.

Containers containing samples of each of the thus prepared suspensions were stored undisturbed at room temperature for 17 days to determine if any sedimentation occurs.

Additional containers containing samples of each of the thus prepared suspensions were stored undisturbed at 40° C. for 17 days to determine if any sedimentation occurs.

Other containers containing samples of each of the thus prepared suspensions were cycled for periods of 24 hours between being placed in a freezer at −29° C. and room temperature for a period of 17 days to determine if any sedimentation occurs.

The amount of sedimentation was determined by measuring any top liquid layer which appeared as the cis compound settled to the bottom. The results of this determination are set forth below in Table 8 for 30 weight percent solutions of cis-1-(3-chloroallyl)-3,5,7-triaza-1-azoniaadamantane chloride and Table 9 for 40 weight percent solutions of cis-1-(3-chloroallyl)-3,5,7-triaza-1-azoniaadamantane chloride.

TABLE 8

Particle settling in percent for compositions of 30 weight percent solutions of cis-1-(3-chloroallyl)-3,5,7#triaza-1-azoniaadamantane chloride in IGEPAL CO-630 in admixture with various thixotropes held under the given storage conditions

| THIXOTROPE | ROOM TEMPERATURE | 40° C. STORAGE | FREEZE/THAW CYCLING |
|---|---|---|---|
| AEROSIL R202 (1%) | no settling | no settling | no settling |
| AEROSIL R805 (2%) | no settling | no settling | no settling |
| FLOWTONE R (2%) | no settling | no settling | no settling |
| THIXCIN R (2%) | no settling | no settling | no settling |
| THIXATROL ST (2%) | no settling | no settling | no settling |
| NO THIXOTROPE CONTROL | 5–6 mm top liquid layer | 2–3 mm top liquid layer | 3 mm top liquid layer |

TABLE 9

Particle settling in percent for compositions of 40 weight percent solutions of cis-1-(3-chloroallyl)-3,5,7-triaza-1-azoniaadamantane chloride in mineral oil in admixture with various thixotropes held under the given storage conditions

| THIXOTROPE | ROOM TEMPERATURE | 40° C. STORAGE | FREEZE/THAW CYCLING |
|---|---|---|---|
| BENTONE 27 (3%) | no settling | no settling | no settling |
| TBOYTHIX XYZ (2%) | no settling | no settling | no settling |
| SYNCROWAX HRS-C (5%) | 1 mm top liquid layer | 1 mm top liquid layer | no settling |
| NO THIXOTROPE CONTROL | 1 mm top liquid layer | 6 mm top liquid layer | 1 mm top liquid layer |

EXAMPLE 8

The physical stability (suspension stability) of compositions consisting of either 30 weight percent of the antimicrobial cis-1-(3-chloroallyl)-3,5,7-triaza-1-azoniaadamantane chloride in IGEPAL CO-630 as the carrier liquid or 40 weight percent of cis-1-(3-chloroallyl)-3,5,7-triaza-1-azoniaadamantane chloride in mineral oil as the carrier liquid when mixed with various thixotrope materials is demonstrated by the following procedure.

Solutions of IGEPAL CO-630 in admixture with a predetermined amount of one of the hereinafter set forth thixotrope materials were prepared. To each of the solutions was slowly added an amount of cis-1-(3-chloroallyl)-3,5,7-triaza-1-azoniaadamantane chloride under high shear mixing conditions so as to prepare solutions containing 30 percent by weight of the antimicrobial. A 30 percent by weight solution of cis-1-(3-chloroallyl)-3,5,7-triaza-1-azoniaadamantane chloride in IGEPAL CO-630 containing no thixotrope material was prepared to serve as a control.

Additionally, solutions of mineral oil in admixture with a predetermined amount of one of the hereinafter set forth thixotrope materials were prepared. To each of the solutions was slowly added an amount of cis-1-(3-chloroallyl)-3,5,7-triaza-1-azoniaadamantane chloride under high shear mixing conditions so as to prepare solutions containing 40 percent by weight of the antimicrobial. A 40 percent by weight solution of cis-1-(3-chloroallyl)-3,5,7-triaza-1-azoniaadamantane chloride in mineral oil containing no thixotrope material was prepared to serve as a control.

Twenty-four mL samples of each of the thus prepared suspensions were placed in separate containers and stored undisturbed at room temperature for 6 months to determine if any sedimentation occurred. The rate of sedimentation was determined by measuring any top liquid layer which appeared as the cis compound settled to the bottom. The results of this determination are set forth below in Table 10 for 30 weight percent solutions of cis-1-(3-chloroallyl)-3,5,7-triaza-1-azoniaadamantane chloride and Table 11 for 40 weight percent solutions of cis-1-(3-chloroallyl)-3,5,7-triaza-1-azoniaadamantane chloride as percent settling improvement as compared to the controls at the end of storage periods of 1 week, 1 month and 6 months.

TABLE 10

Percent improvement in particle settling for compositions of 30 percent by weight cis-1-(3-chloroallyl)-3,5,7-triaza-1-azoniaadamantane chloride in admixture with IGEPAL CO-630 and various thixotrope materials at the given wt. % for the indicated time periods over control

| THIXOTROPE | 1 WEEK | 1 MONTH | 6 MONTHS |
|---|---|---|---|
| AEROSIL R202 (1 wt. %) | 100 | 100 | 100 |
| AEROSIL R805 (1 wt. %) | 100 | 100 | — |
| BENTONE 27 (3 wt. %) | 100 | 50 | 8 |
| BENTONE 34 (3 wt. %) | 100 | 100 | 33 |
| BENTONE 38 (3 wt. %) | 100 | 100 | 58 |
| BENTONE GEL MI0 (3 wt. %) | 100 | 100 | 33 |
| CLAYTONE HT (3 wt. %) | 100 | 142 | 8 |
| CLAYTONE APA (3 wt. %) | 100 | 100 | 67 |
| FLOWTONE B (1 wt. %) | 100 | 100 | 58 |
| SYNCROWAX HRS-C (5 wt. %) | 77 | 50 | 50 |
| THIXCIN R (1 wt. %) | 100 | 100 | 58 |
| THIXATROL ST (1 wt. %) | 100 | 100 | 95 |
| TROYTHIX XYZ (2 wt. %) | 100 | 100 | 50 |
| NO THIXOTROPE CONTROL | 12 mm[1] | 12 mm[1] | 12 mm[1] |

[1]milliliters of liquid rising to top of CONTROL solution

TABLE 11

Percent improvement in particle settling for compositions of 140 percent by weight cis-1-(3-chloroallyl)-3,5,7-triaza-1-azoniaadamantane chloride in admixture with mineral oil and various thixotrope materials at the given wt. % for the indicated time periods over control

| THIXOTROPE | 1 WEEK | 1 MONTH | 6 MONTHS |
|---|---|---|---|
| BENTONE 27 (3 wt. %) | 100 | 100 | 100 |
| BENTONE 34 (3 wt. %) | 100 | 58 | 58 |
| BENTONE 38 (3 wt. %) | 100 | 58 | 42 |
| BENTONE GEL MI0 (3 wt. %) | 100 | 50 | 33 |
| CLAYTONE HT (3 wt. %) | 100 | 58 | 42 |
| CLAYTONE APA (3 wt. %) | 100 | 58 | 50 |
| FLOW TONE R (1 wt. %) | 67 | 50 | 50 |
| SYNCROWAX HRS-C (5 wt. %) | 100 | 100 | 100 |
| THIXCIN R (1 wt. %) | 58 | 42 | 33 |
| THIXATROL ST (1 wt. %) | 100 | 100 | 100 |
| TROYTHIX XYZ (2 wt. %) | 100 | 100 | 100 |
| NO THIXOTROPE CONTROL | 12 mm[1] | 12 mm[1] | 12 mm[1] |

[1]milliliters of liquid rising to top of CONTROL solution

The compositions of the present invention comprising quaternaries 1-(benzyl)-3,5,7-triaza-1-azoniaadamantane chloride, 1-(3-chloroallyl)-3,5,7-triaza-1-azoniaadamantane chloride and the cis- and cis/trans-isomers thereof, 1-(α-(2-xylyl))-3,5,7-triaza-1-azoniaadamantane chloride and methyl 1-(3,5,7-triaza-1-azoniaadamantane chloride) acetate, as the active antimicrobial material, in admixture with an anhydrous carrier liquid and a thixotropic material as an anti-settling agent have all been found to have substantially the same antimicrobial activity as the freshly prepared admixture of the active material in a conventional polar solvent. It is to be further understood that slight differences in composition properties can result from the use of different anhydrous carrier liquids or thixotropic material or from the choice of specific mixtures of the anhydrous carrier liquids and thixotropic materials.

Various modifications may be made in the present invention without departing from the spirit or scope thereof as will be apparent to those skilled in the art.

What is claimed is:

1. An anhydrous, liquid, antimicrobial composition, comprising:
   (a) from about 30 to about 50 percent by weight of a quaternary compound selected from the group consisting of 1-(benzyl)-3,5,7-triaza-1-azoniaadamantane chloride, 1-(3-chloroallyl)-3,5,7-triaza-1-azoniaadamantane chloride as the cis-isomer or a mixture of the cis-isomer and the trans-isomer thereof, 1-(α-(2-xylyl))-3,5,7-triaza-1-azoniaadamantane chloride and methyl 1-(3,5,7-triaza-1-azoniaadamantane chloride) acetate;
   (b) from about 25 to about 70 percent by weight of an anhydrous carrier liquid which does not reduce the amount of antimicrobial activity of the quaternary compound or cause the Gardner color of the composition to be more than 3 during storage under room temperature conditions for time periods of up to six months. the anhydrous carrier liquid being selected from the group consisting of PPG-5-laureth-5, isosteareth-10, PEG-20 corn glyceride, methyl gluceth-20, laureth-9, oleth-3, nonylphenoxypoly(ethyleneoxy) ethanol, PEG 400 monolaurate, PEG 1200 castor oil, PEG 400 dilaurate, $C_{11}$–$C_{15}$ secondary alcohol ethoxylates, caprylic/capric triglyceride, Polyglycol, polysorbate-20, tripropylene glycol methyl ether, mineral oil, lanolin oil, safflower oil, propylene carbonate, toluene and acetone; and
   (c) from about 0.1 to about 10 percent by weight of a thixotropic material which does not cause a reduction of antimicrobial activity of the quaternary compound and retards substantial settling of the composition during storage under room temperature conditions for time periods of up to six months.

2. The antimicrobial composition of claim 1 wherein the quaternary compound is 1-(benzyl)-3,5,7-triaza-1-azoniaadamantane chloride.

3. The antimocrobial composition of claim 1 wherein the quaternary compound is 1-(3-chloroallyl)-3,5,7-triaza-1-azoniaadamantane chloride as the cis-isomer or a mixture of the cis-isomer and the trans-isomer thereof.

4. The antimicrobial composition of claim 3 wherein the 1-(3-chloroallyl)-3,5,7-triaza-1-azoniaadamantane chloride is in the cis-form.

5. The antimicrobial composition of claim 1 wherein the quaternary compound is 1-(α-(2-xylyl))-3,5,7-triaza-1-azoniaadamantane chloride.

6. The antimicrobial composition of claim 1 wherein the quaternary compound is methyl 1-(3,5,7-triaza-1-azoniaadamantane chloride) acetate.

7. The antimicrobial composition of claim 1 wherein the thixotropic material is a fumed silica.

8. The antimicrobial composition of claim 1 wherein the thixotropic material is an organically modified smectite clay.

9. The antimicrobial composition of claim 1 wherein the anhydrous carrier is tripropylene glycol methyl ether.

* * * * *